United States Patent
Kalder et al.

(10) Patent No.: US 10,143,369 B2
(45) Date of Patent: Dec. 4, 2018

(54) METHOD FOR REPRESENTING OPTOTYPES, OPTOTYPE REPRESENTATION, ASSOCIATED USE AND IMAGE OUTPUT DEVICE

(71) Applicants: IPRO GMBH, Leonberg (DE); Dieter Kalder, Moerfelden-Walldorf (DE); Fritz Passmann, Dortmund (DE)

(72) Inventors: Dieter Kalder, Moerfelden-Walldorf (DE); Fritz Passmann, Dortmund (DE)

(73) Assignee: IPRO GmbH, Leonberg (DE)

( * ) Notice: Subject to any disclaimer, the term of this patent is extended or adjusted under 35 U.S.C. 154(b) by 147 days.

(21) Appl. No.: 15/039,587

(22) PCT Filed: Nov. 17, 2014

(86) PCT No.: PCT/EP2014/074805
§ 371 (c)(1),
(2) Date: Dec. 19, 2016

(87) PCT Pub. No.: WO2015/078720
PCT Pub. Date: Jun. 4, 2015

(65) Prior Publication Data
US 2017/0164822 A1    Jun. 15, 2017

(30) Foreign Application Priority Data
Nov. 28, 2013  (DE) .................... 20 2013 010 668 U (51) Int. Cl.
*A61B 3/032*        (2006.01)
*A61B 3/028*        (2006.01)
(Continued)

(52) U.S. Cl.
CPC ............ *A61B 3/032* (2013.01); *A61B 3/0041* (2013.01); *A61B 3/022* (2013.01); *A61B 3/028* (2013.01);
(Continued)

(58) Field of Classification Search
CPC ....... A61B 3/032; A61B 3/022; A61B 3/0041; A61B 3/08; A61B 2560/0223
(Continued)

(56) References Cited

U.S. PATENT DOCUMENTS

| | | |
|---|---|---|
| 4,415,243 A | 11/1983 | Carl-Zeiss-Stiftung |
| 5,764,340 A | 6/1998 | Hofeldt |
| 2009/0073386 A1 | 3/2009 | Petito |

FOREIGN PATENT DOCUMENTS

| | | |
|---|---|---|
| CN | 102764106 A | 11/2012 |
| CN | 202776260 U | 3/2013 |

(Continued)

OTHER PUBLICATIONS

English Abstract for DE 20 2012 000 103 U1.
(Continued)

*Primary Examiner* — Tuyen Tra
(74) *Attorney, Agent, or Firm* — Ware, Fressola, Maguire & Barber LLP (57) ABSTRACT

Method for optotype representation (2) via an image output device (4) for a visual acuity test and/or determination of a refraction, with optotypes (10) being displayed in a three-dimensional image (6) and an image separation occurring in such a way that the optotypes (10) are monocularly discernible in binocular conditions, wherein the three-dimensional image (6) is binocularly discernible.

18 Claims, 7 Drawing Sheets

(51) Int. Cl.
  *A61B 3/08* (2006.01)
  *A61B 3/00* (2006.01)
  *A61B 3/02* (2006.01)

(52) U.S. Cl.
  CPC ........ *A61B 3/08* (2013.01); *A61B 2560/0223* (2013.01)

(58) Field of Classification Search
  USPC .................. 351/201, 200, 41, 205, 211, 222
  See application file for complete search history.

(56) References Cited

FOREIGN PATENT DOCUMENTS

| DE | 202012000103 U1 | 3/2012 |
| EP | 0830839 A2 | 3/1998 |
| GB | 2281634 A | 3/1995 |

OTHER PUBLICATIONS

Using Stereoscopic 3D Technologies for the Diagnosis and Treatment of Amblyopia in Children.
Abstract for Using Stereoscopic 3D Technologies for the Diagnosis and Treatment of Amblyopia in Children, submitted on Sep. 28, 2011.
English Language Abstract of CN102764106A.
English Language Abstract of CN202776260U.

METHOD FOR REPRESENTING OPTOTYPES, OPTOTYPE REPRESENTATION, ASSOCIATED USE AND IMAGE OUTPUT DEVICE

BACKGROUND OF THE INVENTION

1. Field of the Invention

The invention concerns a method for optotype representation via an image output device for a visual acuity test and/or the determination of a refraction. The invention also concerns a respective optotype representation, an image output device and the use of an optotype representation.

2. Brief Description of Related Art

In order to investigate refraction or the visual acuity of human eyes, usually first the first eye is tested while the second eye is covered. Then the second eye is tested while the first eye is covered. This procedure takes a relatively long time, and in addition, the test person's eyes suffer from fatigue during the eyesight test procedure, which may result in measuring errors. In this so-called monocular eye test, zyclophorous (rolling) eyes may occur which then lead to erroneous cylinder values.

SUMMARY OF THE INVENTION

The invention has the purpose of remedying the disadvantages of the state of the art. This task is solved with a method for optotype representation via an image output device for a visual acuity test and/or determination of a refraction, characterized in that optotypes are displayed in a three-dimensional image and an image separation occurs in such a way that the optotypes are monocularly discernible in binocular conditions, wherein the three-dimensional image is binocularly discernible. It is therefore provided that optotypes are presented in a three-dimensional image and that image separation occurs in such a way that the optotypes are discernible monocularly and under binocular conditions, with the three-dimensional image being binocularly discernible. Other advantageous embodiments of the invention result from other features set forth herein.

The fact that provisions are made for both eyes perceiving a three-dimensional binocular image at the same time, but only one eye monocularly discerns the respective optotype effectively prevents eye fatigue and the resulting erroneous test result since relaxed, natural vision is made possible. The entire visual apparatus of the human being including its highest developed form, three-dimensional, stereoscopic vision, is addressed and natural vision during an eyesight test is allowed as much as possible. This allows particularly advantageous eyesight tests and thus eventually glasses with a correction that is particularly advantageous for spectacle wearers. It is furthermore no longer necessary to interrupt binocular vision by a covering plate or similar in order to conduct a monocular eyesight test. Instead, both eyes always see during the entire eyesight test procedure, while at the same time the optotypes are discernible monocularly. Thus, all necessary functions of a pair of eyes can be tested binocularly under monocular arrangement, with the disadvantages of monocular eyesight tests, especially eye fatigue and unnatural vision with just one eye are effectively avoided, which leads to more exact and agreeable spectacle corrections. The image output device may also be a 3D monitor or a 3D TV. Such an image output device allows an optotype representation in a particularly simple manner since it is not necessary, for example for an optician, to buy expensive special instruments for conducting eyesight tests. It is also conceivable that filters with circulating polarization or shutter glasses are used for image separation. Especially in cases in which the image output device is a 3D TV, this allows provision of a particularly easy and cost-effective method for optotype representation. In passive 3D technology, for example, the 3D effect is achieved by linear circular polarization, with 3D glasses being used for image separation.

It is advantageous if the three-dimensional image extends to the vertical edges of the image and/or the image output device. This allows provision of a peripheral fusion stimulus by a three-dimensional image being displayed on the entire width of the image output device, which means further approximation of natural, stereoscopic vision.

It is conceivable that the optotypes are arranged in a horizontal line. It is furthermore also conceivable that several such lines are arranged vertically one on top of another. This especially allows conducting eyesight tests that use several optotypes. Furthermore, this allows conducting several eyesight tests with just one optotype representation.

It is furthermore conceivable that an optotype chart is displayed in the three-dimensional image, with the optotypes being arranged within the optotype chart. It is therefore possible to display the optotype charts so far used for visual acuity tests together with the optotypes in a three-dimensional image.

The initially stated purpose is also solved by an optotype representation provided according to the method according to the invention. Such an optotype representation is especially characterized by the fact that optotypes can be discerned monocularly in binocular conditions during a visual acuity test and/or the determination of a refraction, with a three-dimensional image being binocularly discernible and with optotypes being discernible monocularly in the three-dimensional image. Furthermore, the initially stated task is also solved by an image output device, set up for an optotype representation according to the invention. The image output device may comprise a 3D monitor or 3D TV. In order to set up the image output device for an optotype representation according to the invention, especially a control unit such as, for example, a computer, a tablet computer, a laptop or a smartphone is used, with the control unit having software that allows controlling the image output device in such a way that the image output device outputs an optotype representation according to the invention.

Finally, the initially stated task is also solved by using an optotype representation according to the invention for an eyesight test. Such an eyesight test may especially be a visual acuity test and/or the determination of a refraction.

The eyesight test may also be a binocular fine tuning or a dominance test.

Preferably, the optotype representation used displays optotypes in a horizontal line in such a way that three different visual tests can be conducted. A first and a second of the three eyesight tests may be a screening of contrast sensitivity and cylinder refraction. This allows checking the functions of the pair of eyes in a particularly short time binocularly with a monocular assignment. It has proven particularly advantageous if the optotype representation is used in a stereo test. The optotypes are stereoscopically perceived during the eyesight test and may, for example, also be arranged in a certain stereo angle.

The invention is further distinguished by the following:

The invention concerns an optotype representation via an image output device (e.g. 3D monitor or 3D TV) that shows three-dimensional images that are intended for the subjective refraction of humans.

In the procedure according to the state of the art to determine refraction, first one eye was examined while the other eye was covered, then vice versa. The second eye was added at a later time. Due to the relatively long procedure involved, the patient's eyes tire during the process which may lead to errors in the measurement. In addition, this so-called monocular test may generate zyclophorous (rolling) eye positions that may lead to an erroneous correction of the cylinder values.

The invention has the purpose of providing a method for refraction determination that avoids measuring errors due to eye fatigue and due to a zyclophorous eye condition.

Optotypes in a three-dimensional environment are shown on a 3D monitor or 3D TV device with circular polarization. Filters with circular polarization are used that allow simultaneous monocular vision of the eyes in binocular conditions. The new element of this method is that the entire visual organ sees a 3D image in the background, but the respective optotype is only presented to one eye. This allows addressing the complete visual organ of the human being including its highest developed form, stereoscopic vision, and natural, complete vision is demanded. This obtains a refraction result that corresponds to normal, natural vision. In this process, both eyes of the test person remain open from the beginning. This refraction option allows particularly precise corrections that are especially necessary for compatible spectacle corrections, especially for comfortable varifocal glasses. The advantage of this method is that all the necessary functions of the pair of eyes are tested binocularly with monocular assignment in a very short time.

The invention is further distinguished by the fact that optotypes are represented in a three-dimensional image for the entire course of a visual acuity test. The invention is further characterized by the patient being able to see the optotypes to determine the refraction (refraction process) during the test with both eyes simultaneously monocularly under binocular conditions. During the entire refraction procedure, binocular vision no longer has to be prevented by a covering plate. Both eyes always see simultaneously, although different images as required. Representation may occur on a 3D monitor or another suitable device. The separation of the visual impressions takes place by circularly polarizing separation procedures.

In addition to the previous tests, new tests have been developed:
a. Stereo test in a 3D environment;
b. Dominance test to determine the dominating eye;
c. Optotype chart with 3 different tests;
d. Optotypes for a binocular fine-tuning in a 3D environment without any additional background.

BRIEF DESCRIPTION OF THE DRAWING

Other advantages and advantageous embodiments of the inventions arise from the following description that describes and explains the embodiments shown in the drawing in detail, as follows.

DETAILED DESCRIPTION OF THE BEST MODE OF THE INVENTION

Figure 1:
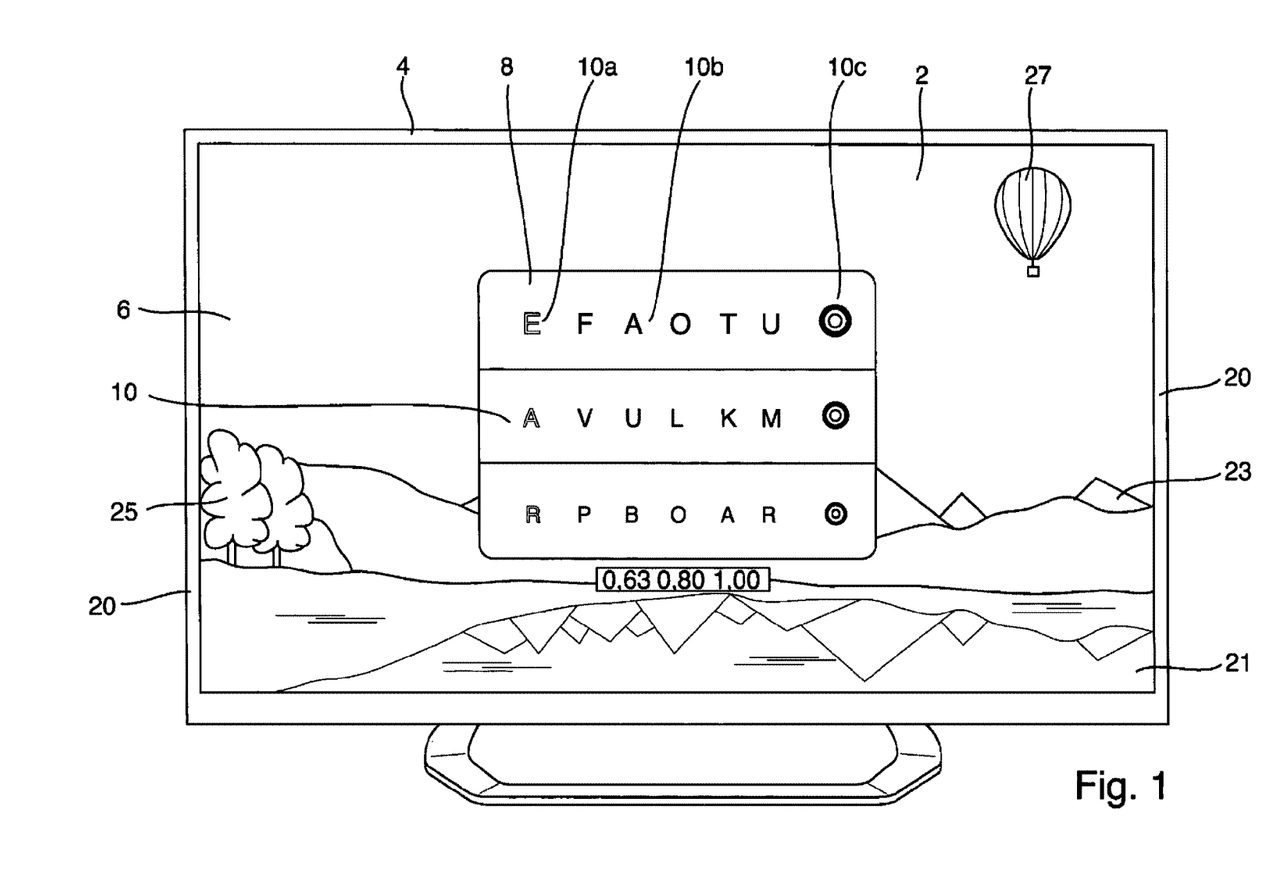
FIG. 1: Image output device according to the invention, set up for optotype representation.

FIG. 1 shows an image output device 4 for a visual acuity test and/or the determination of a refraction, said device being set up for optotype representation 2. The image output device 4 comprises a 3D TV with differently polarized light being emitted in each row, so that the optotype representation 2 consists of the superposition of two fields 5, 7—shown in FIG. 2.

Figure 2:
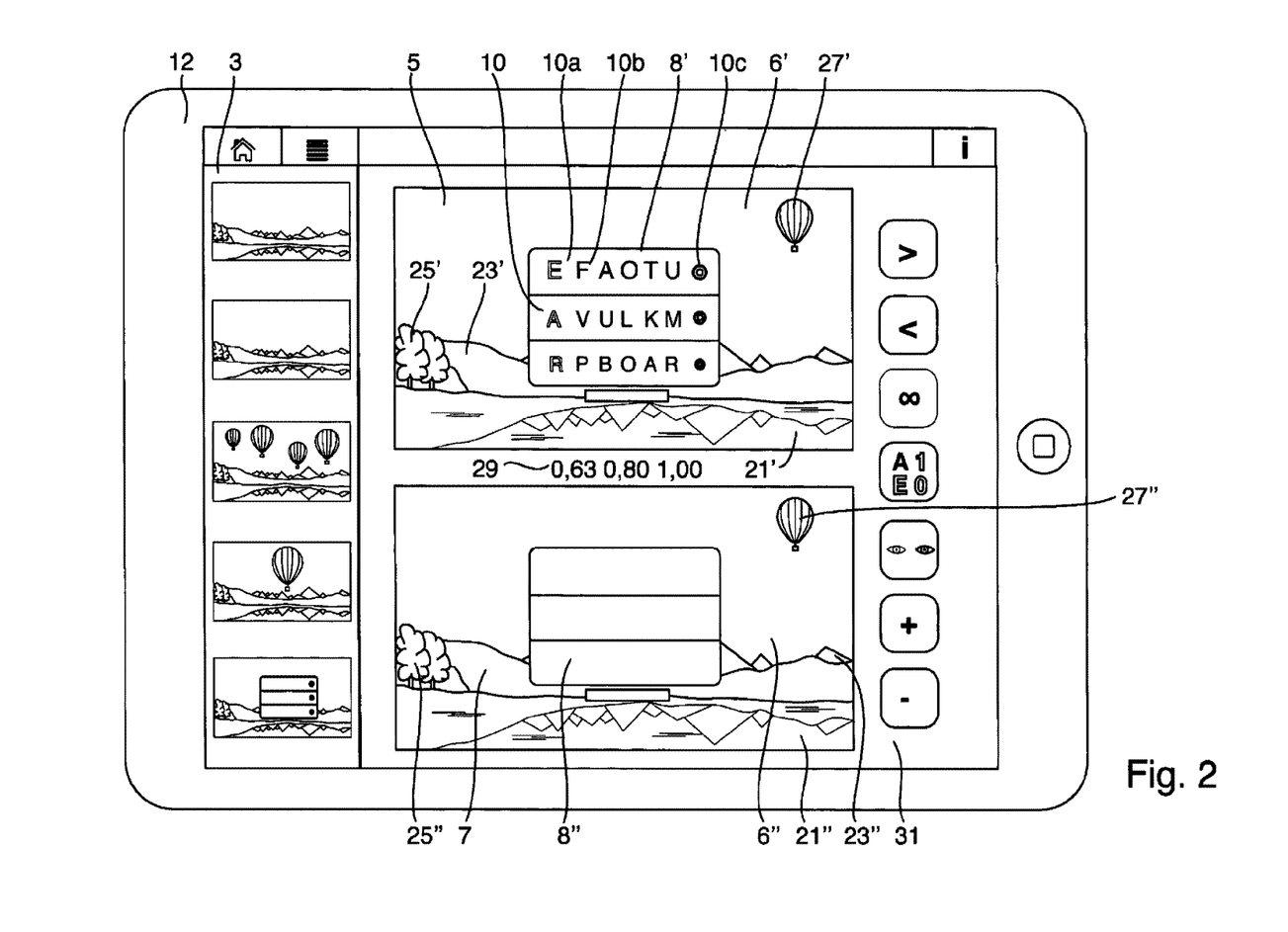
FIG. 2: Control unit for controlling the image output device according to the invention.

FIG. 2 shows a control unit in the form of a tablet computer 12 to control the image output device 4, with the tablet computer 12 having a software to control the image output device 4. According to the FIGS. 1 and 2, the first field 5 comprises a first image section 6' showing a landscape with a lake 21', mountains 23', trees 25' and a hot air balloon 27'. Within the first image section 6', there is an optotype chart 8, with optotypes 10 being arranged in the form of a relatively large letter "E" 10a, in the form of five smaller letters "F, A, O, T, U" 10b and in form of a circular FIG. 10c in a horizontal line within the optotype chart 8. The second line below this one contains smaller optotypes compared to the first line, in the form of a relatively large letter "A" 10a, in the form of five smaller letters "V, U, L, K, M" 10b and in the form of a circular FIG. 10c in a horizontal line. Below this one in a third line, once again optotypes that are smaller compared to the second line are arranged, in the form of a relatively large letter "R" 10a, in the form of five smaller letters "P, B, O, A, R" 10b and in the form of a circular FIG. 10c in a horizontal line. The size relation of the individual lines can be understood from the parameters 29.

The second field 7 also has a first image section 6" showing a landscape with a lake 21", mountains 23", trees 25" and a hot air balloon 27", with the first image section 6" corresponding to the first image section 6' of the first field 5. Within the first image section 6" there is furthermore an optotype chart 8" arranged that corresponds to the optotype chart 8' of the first field 5. However, the second image section 7 does not have any optotypes.

A person conducting the eyesight test may—as indicated by the selection bar 3—select which three-dimensional image 6 and which type of optotypes 10 should be displayed on the image output device 4. Furthermore, the tablet computer 12 is used to select whether the first field 5 and/or the second field 7 shows or show optotypes 10. Finally, the size of the optotypes 10 may, for example, be modified by means of the control keys 31.

Figure 3:
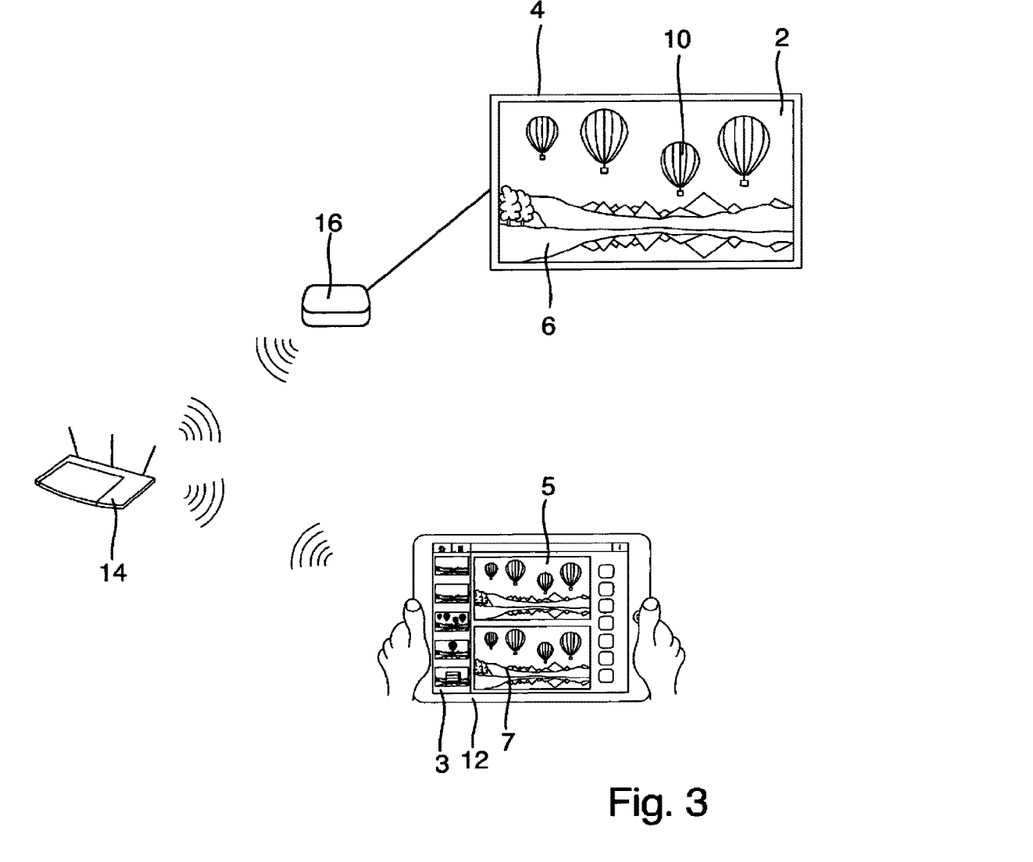
FIG. 3: Schematic representation of a system with the control unit according to FIG. 2 to set up the image output device according to the invention.

As shown in FIG. 3, the image output device 4 is controlled wirelessly via the tablet computer 12 by control signals that are transmitted to a receiver 16 on the image output device 4 through a router 14. On the image output device 4, the first field 5 and the second field 7 are displayed line sequentially. Consequently, the image output device 4 displays an optotype representation 2 that consists of two fields 5, 7.

In order to conduct the method for optotype representation, an image separation by means of 3D glasses is further provided. The first field 5 of the optotype representation 2 is only discernible for the left eye, while the second field 7 of the optotype representation 2 is only discernible for the right eye, wherein the brain fuses the two visual impressions from the left and right eye into one visual impression.

If the stereoscopic visual faculty of a test person is intact, the brain unites the first image section 6' of the first field 5 and the first image section 6" of the second field 7 into a three-dimensional image 6 showing a landscape with a lake 21, mountains 23, trees 25 and a hot air balloon 27. The optotype chart 8' of the first field 5 and the optotype chart 8" of the second field 7 are united into one optotype chart 8.

The optotypes 10a, 10b and 10c of the first field 5 according to FIG. 2 are only discernible for the left eye and therefore are not stereoscopically perceived even after the visual impressions from the left and right eye are fused into one visual impression due to the only monocular perception. The optotype representation 2 hence allows conducting an eyesight test, with the three-dimensional image of a landscape with a lake 21, mountains 23, trees 25 and a hot air balloon 27 being discernible binocularly while the optotypes 10a, 10b, 10c are discernible monocularly under binocular conditions.

This allows a largely relaxed, natural seeing process during an eyesight test. Eye fatigue and the resulting distorted test result can be effectively prevented.

According to FIG. 1, the three-dimensional image 6 extends to the vertical edges 20 of the screen of the image output device 4, thus providing a peripheral fusion stimulus.

Further features of the invention result from the following description of eyesight tests that are conducted using an optotype representation 2 and allow a rational, fast eyesight test process:

FIGS. 4 to 7 each show a first field 5 with a first image section 6' and a second field 7 with a second image section 6", wherein the second image section 6" corresponds to the first image section 6'.

Figure 4:
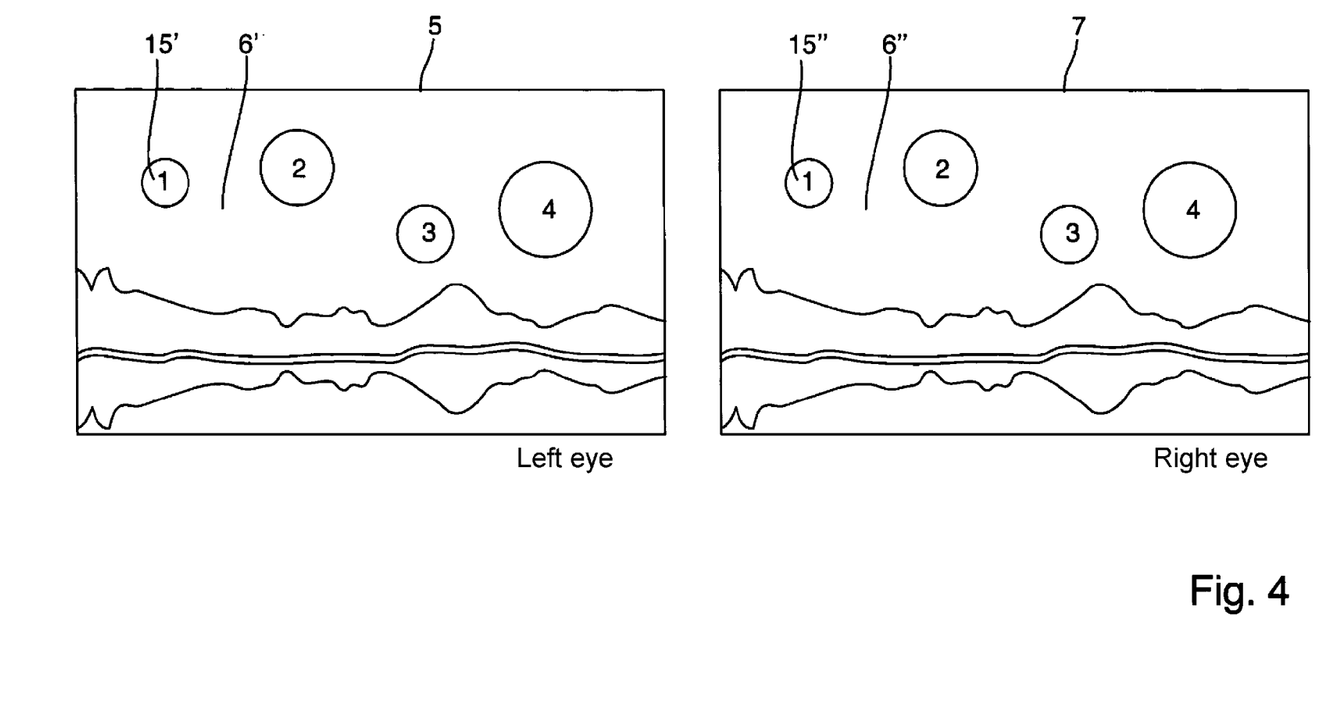
FIG. 4: First and second field of an optotype representation according to the invention for binocular fine tuning.

According to FIG. 4, the first field 5 comprises optotypes 15' in the form of numbered balloons with the numbers 1 to 4. The second field 7 also comprises optotypes 15" in the form of numbered balloons with the numbers 1 to 4. The optotypes 15' and 15" are arranged at a certain stereo angle to each other in this. This tests the spatial vision of a test person. In order to permit spatial vision, the two visual impressions from the left and the right eye must be able to be fused into a single visual impression. A stereo test according to FIG. 4 allows the test of whether the test person's visual system allows stereoscopic vision since in this case not only the three-dimensional image 6, but also the optotypes shaped like balloons 1 to 4 are stereoscopically discernible. In case of stereopsis, the balloons with the numbers 1 and 2 appear to be in the background while the balloons numbered 3 and 4 seem to be approaching the test person and appear within one's reach.

Figure 5:
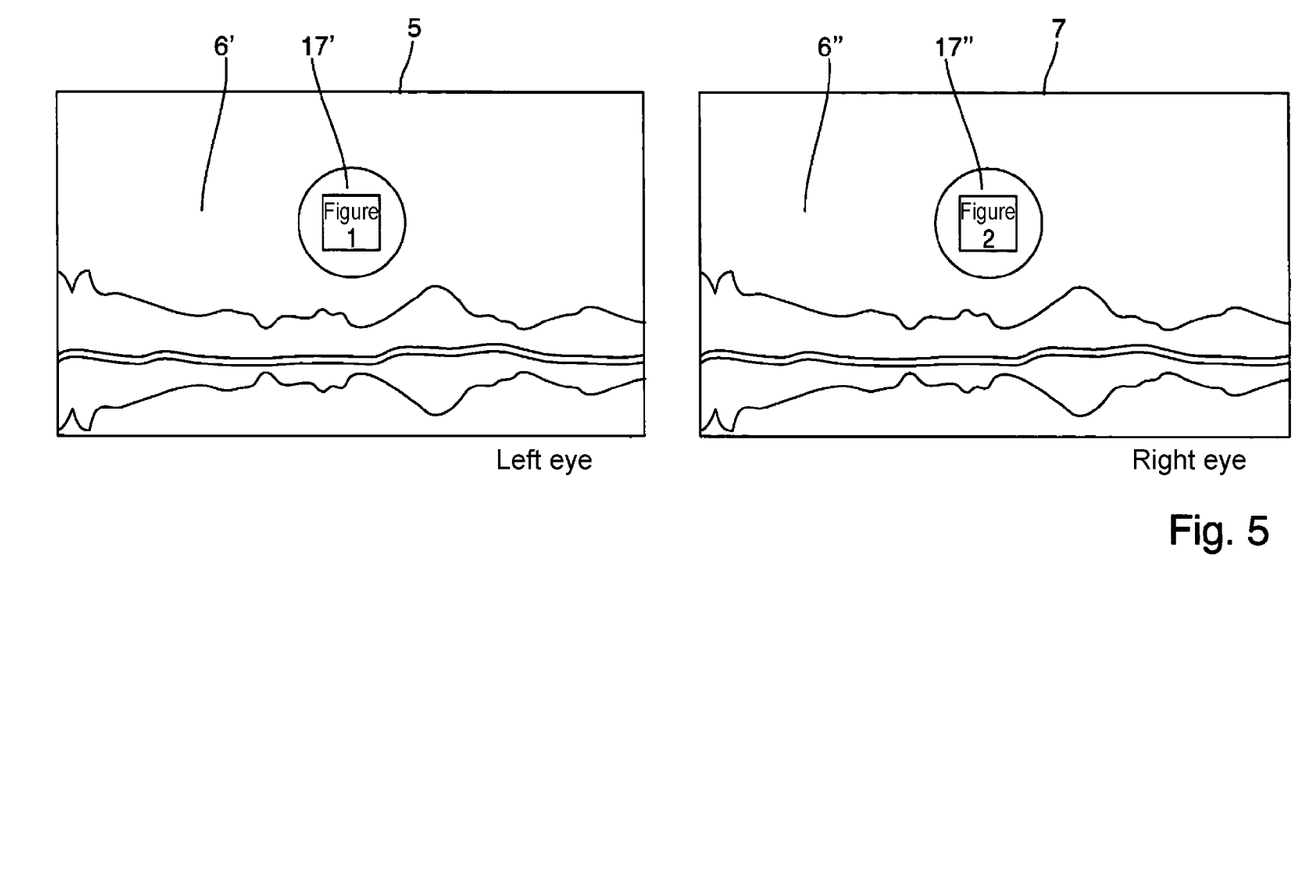
FIG. 5: First and second field of an optotype representation according to the invention with an optotype chart that shows optotypes for various eyesight tests.

FIG. 5 shows a first and a second field 5, 7 for an optotype representation 2 to be used in a dominance test. The first field 5 contains an optotype shaped as "FIG. 1" 17' within a "hot air balloon 1", with "FIG. 1" being, for example, a dog. The second field 7 contains an optotype shaped as "FIG. 2" 17" within a "hot air balloon 2", with "FIG. 2" being, for example, a cat. Using an optotype representation 2, "FIG. 1" 17' is only discernible to the left eye, while "FIG. 2" 17" is only discernible to the right eye. A human regularly has one dominant eye, so that the visual impression of a test person is such that "hot air balloon 1" and "hot air balloon 2" are fused into a stereoscopically perceived hot air balloon. However, the test person's brain fuses the visual impressions from the left and the right eye into one visual impression in such a way that either "FIG. 1" 17' or "FIG. 2" 17" are perceived. This dominance test therefore can be used to test which eye is the dominant eye for seeing.

Figure 6:
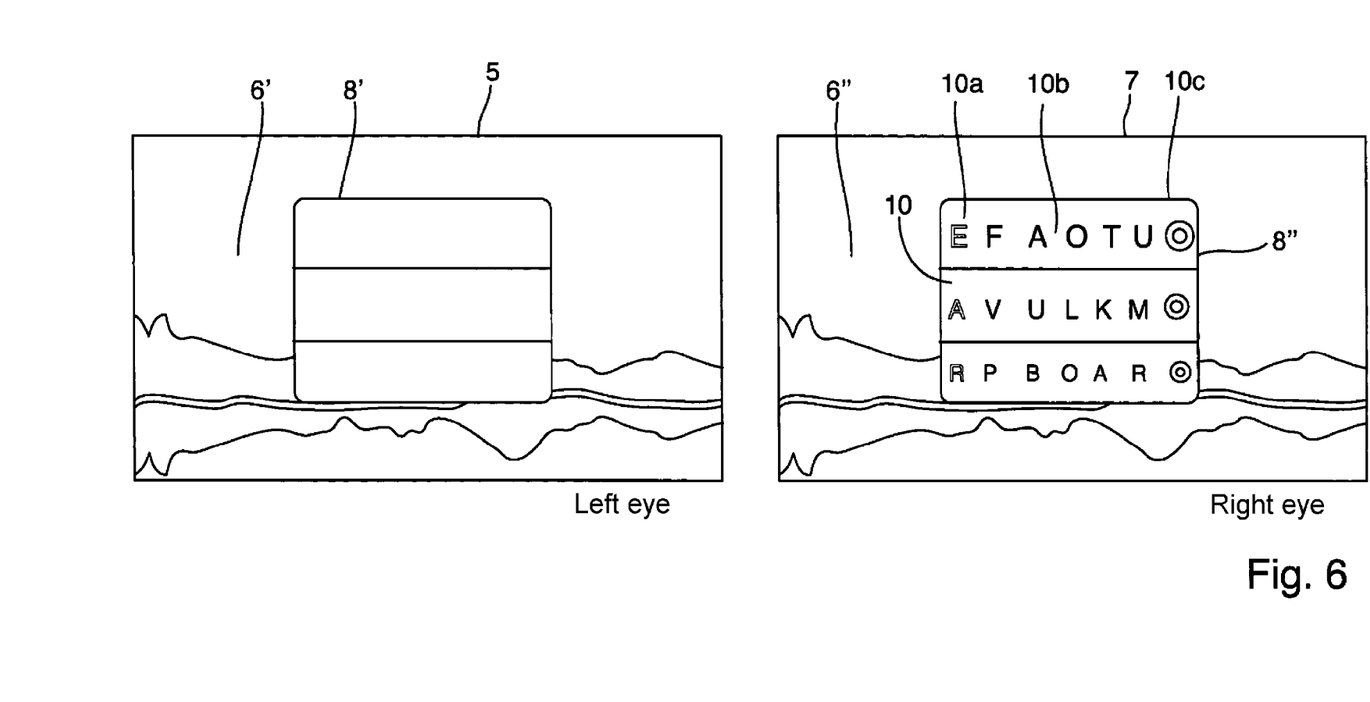
FIG. 6: First and second field of an optotype representation according to the invention for conducting a stereo test.

FIG. 6 shows a first field 5 and a second field 7 as they are also shown in FIG. 2. Using an optotype representation 2 as shown in FIG. 1, three different eyesight tests may be conducted by means of that one optotype representation 2. The optotypes 10a, 10b, and 10c are only discernible to the right eye. The first optotype in the form of the letter 10a serves to screen contrast vision while the other five optotypes 10b are used for a visual test that itself is known from prior art, and the circular FIG. 10c is used to measure cylinder refraction. When an eyesight test is conducted, the top line of the optotype representation 2 according to FIG. 1 from the first optotype 10a to the last optotype 10c is used to check whether certain features of the optotypes 10 are recognized. Then, the second line from the optotype chart 8 is tested, with the optotypes 10 being smaller than the optotypes 10 from the first line. Finally, the eyesight test is continued with the third line, with the optotypes 10 in this line once again being smaller than the optotypes 10 in the second line. The use of an optotype representation 2 constructed from the first field 5 and the second field 7 according to FIG. 7 serves to conduct a binocular fine tuning process. The first field 5 contains a fusion element 18' and the second field 7 a fusion element 18" for this, with the fusion elements 18', 18" being discernible binocularly as a central fusion element using the optotype representation 2. This allows testing visual characteristics of the left and the right eye by means of a single optotype representation 2. It is therefore obsolete to use two separate optotype representations to test the visual characteristics of the left eye and/or the right eye. When such an eyesight test is performed, it is possible, for example, to first test the first line of the optotypes 12a, 12b of field 5 discernible by the left eye, with first the first optotype 12a shaped as a circular figure being tested, and then the test being continued with the five optotypes in the form of the letters 12b. Then, the test may be continued with lines two to four of the field 5, or the test first continues with the first line of the optotypes 19a, 19b of the field 7 that is discernible with the right eye, with first the optotypes shaped as a circular FIG. 19b being tested, and then the test being continued with the five optotypes in the form of the letters 19a.

The invention is further distinguished by the following:

FIG. 4 shows a left and a right image that are united into a 3D image on the output monitor. The landscape and the hot air balloons are seen stereoscopically. The hot air balloons are optotypes that are arranged in a certain stereo angle.

FIG. 5 shows a dominance test. The test shows which eye is the dominant eye for seeing. The hot air balloons are different on the left and right, each showing a different image (e.g. animal).

FIG. 6 shows an optotype chart in the 3D environment. The visual check contains three different tests. The first letter serves to screen contrast vision, the other five are normal optotypes, the circular figure serves for cylinder refraction.

Figure 7:
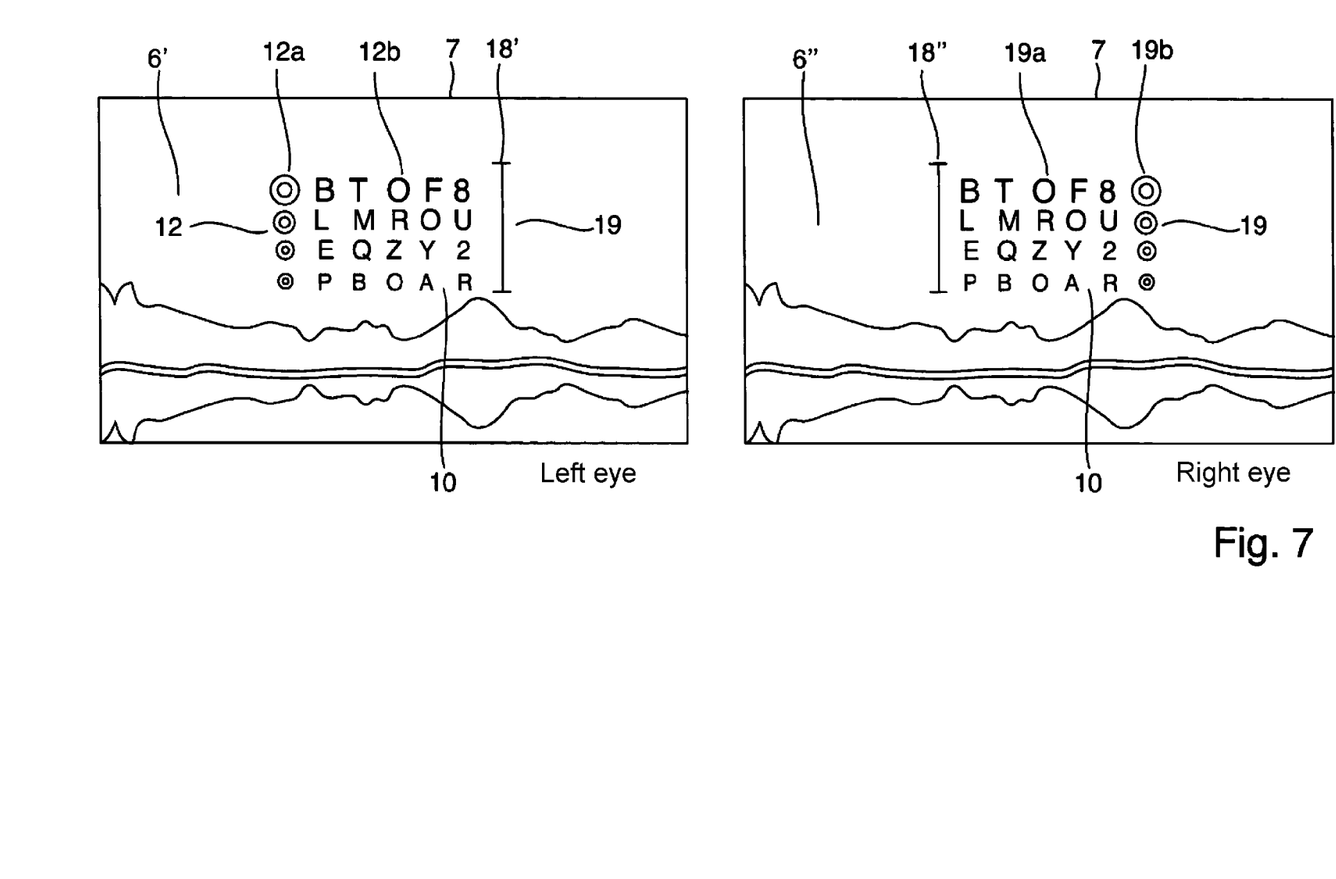
FIG. 7: First and second field of an optotype representation according to the invention for conducting a dominance test.

FIG. 7 serves for a binocular fine tuning and shows optotypes only in a 3D environment without a white background, as in FIG. 3, to allow relaxed vision into the distance.

Scope of the Invention

It should be understood that, unless stated otherwise herein, any of the features, characteristics, alternatives or modifications described regarding a particular embodiment herein may also be applied, used, or incorporated with any other embodiment described herein. Also, the drawing herein is not drawn to scale. Although the invention has been described and illustrated with respect to exemplary embodiments thereof, the foregoing and various other additions and omissions may be made therein and thereto without departing from the spirit and scope of the present invention.

The invention claimed is:

1. Method for optotype representation (2) via an image output device (4) for a visual acuity test and/or determination of a refraction, characterized in that optotypes (10) are displayed in a three-dimensional image (6) constructed from two fields (5, 7) offset against each other by one parallax, so that an image separation occurs in such a way that the optotypes (10) are monocularly discernible in binocular conditions, wherein the three-dimensional image (6) is binocularly discernible and the three-dimensional image is discernible in the background.

2. Method for optotype representation (2) according to claim 1, characterized in that the image output device (4) is a 3D monitor or a 3D TV.

3. Method for optotype representation (2) according to claim 2, characterized in that filters with circular polarization or shutter glasses are used for the image separation.

4. Method for optotype representation (2) according to claim 2, characterized in that the optotype representation (2) is presented in such a way that both eyes always look through a cover glass simultaneously without interruption, even if each eye sees different optotypes (10) at the same time if required.

5. Method for optotype representation (2) according to claim 2, characterized in that the three-dimensional image (6) extends up to the vertically running edges (20) of the image (6) and/or image output device (4).

6. Method for optotype representation (2) according to claim 2, characterized in that the optotypes (10) are arranged in a horizontal line.

7. Method for optotype representation (2) according to claim 1, characterized in that filters with circular polarization or shutter glasses are used for the image separation.

8. Method for optotype representation (2) according to claim 1, characterized in that the optotype representation (2) is presented in such a way that both eyes always look through a cover glass simultaneously without interruption, even if each eye sees different optotypes (10) at the same time if required.

9. Method for optotype representation (2) according to claim 1, characterized in that the three-dimensional image (6) extends up to the vertically running edges (20) of the image (6) and/or image output device (4).

10. Method for optotype representation (2) according to claim 1, characterized in that the optotypes (10) are arranged in a horizontal line.

11. Method for optotype representation (2) according to claim 10, characterized in that several lines are arranged vertically above each other.

12. Method for displaying optotype representation (2) according to claim 1, characterized in that an optotype chart (8) is displayed in the three-dimensional image (6), wherein the optotypes (10) are arranged within the optotype chart (8).

13. Method according to claim 1, wherein the method comprises using the optotype representation (2) in an eyesight test, including for a visual acuity test and/or to determine the refraction.

14. Method according to claim 13, wherein the eyesight test is a binocular fine calibration or a dominance test.

15. Method according to claim 13, wherein the method comprises using the optotypes (10) of one line for three different eyesight tests.

16. Method according to claim 15, wherein a first and a second of the three eyesight tests are a screening of contrast sensitivity and cylinder refraction.

17. Method according to claim 15, wherein the eyesight test is a stereo test, with the optotypes (10) being seen stereoscopically during the eyesight test and/or being arranged in a certain stereo angle.

18. An image output device (4) for displaying optotype representation (2) via for a visual acuity test and/or determination of a refraction, characterized in that the image output device (4) is configured to display optotypes (10) in a three-dimensional image (6) constructed from two fields (5, 7) offset against each other by one parallax, so that an image separation occurs in such a way that the optotypes (10) are monocularly discernible in binocular conditions, wherein the three-dimensional image (6) is binocularly discernible and the three-dimensional image is discernible in the background.

* * * * *